United States Patent
Nakaya et al.

(10) Patent No.: US 9,814,447 B2
(45) Date of Patent: Nov. 14, 2017

(54) ULTRASONIC DIAGNOSTIC APPARATUS

(71) Applicant: TOSHIBA MEDICAL SYSTEMS CORPORATION, Otawara-shi (JP)

(72) Inventors: Shigemitsu Nakaya, Nasushiobara (JP); Mio Azegami, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 848 days.

(21) Appl. No.: 13/919,380

(22) Filed: Jun. 17, 2013

(65) Prior Publication Data

US 2013/0345564 A1  Dec. 26, 2013

(30) Foreign Application Priority Data

Jun. 20, 2012 (JP) ................................ 2012-138551

(51) Int. Cl.
*A61B 8/08* (2006.01)
*A61B 8/00* (2006.01)

(52) U.S. Cl.
CPC ............ *A61B 8/5246* (2013.01); *A61B 8/488* (2013.01); *A61B 8/463* (2013.01)

(58) Field of Classification Search
CPC ......... A61B 8/08; A61B 8/5246; A61B 8/488; A61B 8/463
See application file for complete search history.

(56) References Cited

U.S. PATENT DOCUMENTS

| | | | | |
|---|---|---|---|---|
| 4,182,173 A | * | 1/1980 | Papadofrangakis | ..... A61B 8/00 600/441 |
| 2005/0203401 A1 | * | 9/2005 | Takimoto | ................. A61B 8/06 600/441 |
| 2008/0009727 A1 | | 1/2008 | Kataguchi | |
| 2010/0106021 A1 | | 4/2010 | Li | |
| 2011/0087102 A1 | | 4/2011 | Hamada et al. | |
| 2011/0092819 A1 | | 4/2011 | Takimoto et al. | |

(Continued)

FOREIGN PATENT DOCUMENTS

| | | |
|---|---|---|
| CN | 101081171 A | 12/2007 |
| CN | 100435739 C | 11/2008 |
| CN | 102028500 A | 4/2011 |

(Continued)

OTHER PUBLICATIONS

Combined Office Action and Search Report dated Dec. 3, 2014 in Chinese Patent Application No. 201310245787.3 with English translation.

*Primary Examiner* — Joseph M Santos Rodriguez
(74) *Attorney, Agent, or Firm* — Oblon, McClelland, Maier & Neustadt, L.L.P.

(57) ABSTRACT

According to one embodiment, a transmission processing unit transmits, to a subject via the ultrasonic probe, ultrasonic waves corresponding to a Doppler mode and remaining modes. A reception processing unit receives the ultrasonic wave reflected by the subject via the ultrasonic probe as an echo signal. An ultrasonic image generation unit generates images in the Doppler mode and the remaining modes based on the echo signal. A control unit changes a ratio of transmission of the ultrasonic wave corresponding to the Doppler mode to transmission of the ultrasonic waves corresponding to the remaining modes in accordance with a degree of a pulsatory of the subject.

8 Claims, 11 Drawing Sheets

(56) References Cited

U.S. PATENT DOCUMENTS

2012/0053461 A1    3/2012  Li et al.

FOREIGN PATENT DOCUMENTS

| CN | 102038522 A | 5/2011 |
| CN | 102370499 A | 3/2012 |
| JP | 2001-70304 A | 3/2001 |
| JP | 2005-168585 | 6/2005 |
| JP | 2006-75426 A | 3/2006 |

* cited by examiner

ULTRASONIC DIAGNOSTIC APPARATUS

CROSS-REFERENCE TO RELATED APPLICATIONS

This application is based upon and claims the benefit of priority from Japanese Patent Application No. 2012-138551, filed Jun. 20, 2012, the entire contents of which are incorporated herein by reference.

FIELD

Embodiments described herein relate generally to an ultrasonic diagnostic apparatus that simultaneously displays images in a plurality of modes including a Doppler mode.

BACKGROUND

An ultrasonic diagnostic apparatus is a diagnostic apparatus that displays an image of in vivo information, and is used for noninvasive real-time observation as an inexpensive apparatus without exposure, as compared to other image diagnostic apparatuses such as an X-ray diagnostic apparatus and an X-ray computed tomography apparatus. The ultrasonic diagnostic apparatus has a wide scope and field of application and is applied to diagnosis of a circulatory organ such as a heart, an abdominal organ such as a liver or a kidney, a peripheral blood vessel, obstetrics and gynecology, a breast cancer, and the like.

In general, the ultrasonic diagnostic apparatus transmits an ultrasonic wave into a subject using an ultrasonic probe, and receives a reflected wave from the subject, thereby obtaining diagnostic information (ultrasonic image) in the subject. Examples of the operation modes of the ultrasonic diagnostic apparatus are a B mode (B) to display a two-dimensional morphological image (B-mode image), a color mode (C) to display a two-dimensional blood flow image (color Doppler mode image), and a Doppler mode (D) to display a Doppler waveform (Doppler spectrum image).

One of the modes to display images in a plurality of operation modes in such an ultrasonic diagnostic apparatus is the Triplex mode. According to the Triplex mode, images in, for example, the B mode, the color mode, and the Doppler mode can be displayed simultaneously. Note that in the Triplex mode, two types of scan including interleave scan and segment scan are used.

The interleave scan is a scan method of alternately transmitting ultrasonic waves (beams) corresponding to the B mode, the color mode, and the Doppler mode. In the interleave scan, the quality of an image in the Doppler mode (to be simply referred to as the image quality of the Doppler mode hereinafter) is high, as compared to the segment scan. However, a constraint is placed on the upper limit of the velocity of the blood flow.

On the other hand, the segment scan is a scan method of transmitting an ultrasonic wave corresponding to the Doppler mode continuously for a predetermined period and then transmitting ultrasonic waves corresponding to the B mode and the color mode. Note that according to the segment scan, a Doppler waveform is generated by interpolation when transmitting the ultrasonic waves corresponding to the B mode and the color mode. In the segment scan, the upper limit of the velocity of the blood flow can be set higher than in the above-described interleave scan. However, the image quality of the Doppler mode degrades because the Doppler waveform in the Doppler mode is estimated by interpolation.

To improve the image quality of the Doppler mode in the above-described segment scan, the period (gap period) in which the ultrasonic wave corresponding to the Doppler mode is not transmitted needs to be shorter. In other words, the number of data of the Doppler mode (that is, the transmission count of the ultrasonic wave corresponding to the Doppler mode) is increased. In this case, however, since the number of data of the B mode and the color mode (that is, the transmission count of the ultrasonic waves corresponding to the B mode and the color mode) decreases, the qualities of the images in the B mode and the color mode (to be simply referred to as the image qualities of the B mode and the color mode hereinafter) degrade. For this reason, data distribution to the B mode, the color mode, and the Doppler mode needs to be optimized such that the image qualities of the B mode, the color mode, and the Doppler mode balance depending on, for example, the measurement condition.

To do this, the ultrasonic diagnostic apparatus is provided with a switch called IQ-balance. Using the switch, the examiner (user) can select the Doppler mode, the B mode, or the color mode to emphasize the image quality. For example, to emphasize the image quality of the Doppler mode, the number of data of the Doppler mode is increased to shorten the gap period, thereby improving the image quality of the Doppler mode. On the other hand, to emphasize the image qualities of the B mode and the color mode, the number of data of the Doppler mode is decreased, and the number of data of the B mode and the color mode is increased, thereby improving the image qualities of the B mode and the color mode.

In the ultrasonic diagnosis, various blood flows of a subject can be measured in the Doppler mode. The blood flows measured in the Doppler mode include a pulsating blood flow that temporally changes the flow velocity along with the heartbeat (to be referred to as a pulsating flow hereinafter) and a blood flow having a predetermined flow velocity (to be referred to as a steady flow hereinafter).

If the blood flow to be measured is the pulsating flow, the degradation in the Doppler waveform in the Doppler mode is noticeable. Hence, it is therefore necessary to shorten the gap period by increasing the number of data of the Doppler mode.

On the other hand, if the blood flow to be measured is the steady flow, the degradation in the Doppler waveform in the Doppler mode is relatively small even when the above-described gap period is long.

For this reason, the number of data of the B mode and the color mode (that is, the data distribution in the B mode and the color mode) can be increased.

As described above, the feature of (the degradation in) the Doppler waveform changes between the pulsating flow and the steady flow. However, examination is generally performed without changing the data distribution between the B mode, the color mode, and the Doppler mode depending on whether the blood flow to be measured is the pulsating flow or the steady flow. In addition, the examiner may determine the pulsating flow or the steady flow and change the above-described IQ-balance each time. However, this operation is cumbersome for the examiner.

Hence, there is demanded a mechanism for automatically optimizing the image quality of each operation mode when simultaneously displaying images in a plurality of operation modes including the Doppler mode as in the above-described Triplex mode.

DETAILED DESCRIPTION

In general, according to one embodiment, an ultrasonic diagnostic apparatus according to this embodiment includes an ultrasonic probe, a transmission processing unit, a reception processing unit, an ultrasonic image generation unit, a display unit, a detection unit, and a control unit. The transmission processing unit transmits, to a subject via the ultrasonic probe, ultrasonic waves corresponding to a Doppler mode to display a Doppler waveform representing a time-rate change in a flow velocity value of a blood flow of the subject and remaining modes other than the Doppler mode. The reception processing unit receives the ultrasonic wave reflected by the subject via the ultrasonic probe as an echo signal concerning a scan plane. The ultrasonic image generation unit generates images in the Doppler mode and the remaining modes based on the echo signal. The display unit simultaneously displays the images in the Doppler mode and the remaining modes. The detection unit detects a pulsatory of the blood flow of the subject corresponding to the scan plane. The control unit changes a ratio of transmission of the ultrasonic wave corresponding to the Doppler mode to transmission of the ultrasonic waves corresponding to the remaining modes in accordance with a degree of the detected pulsatory.

Each embodiment will now be described with reference to the accompanying drawings.

(First Embodiment)

Figure 1:
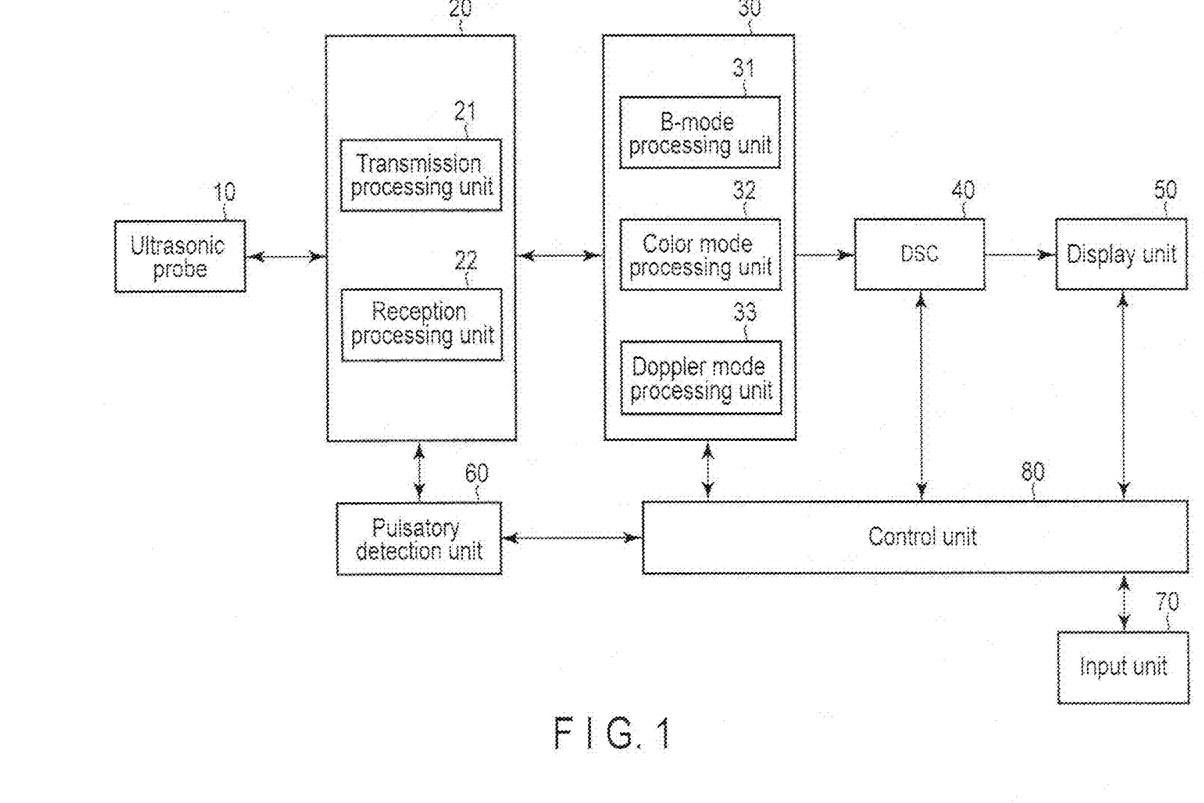
FIG. 1 is a block diagram showing the arrangement of an ultrasonic diagnostic apparatus according to the first embodiment.

An ultrasonic diagnostic apparatus according to the first embodiment will be described first. FIG. 1 illustrates the arrangement of the ultrasonic diagnostic apparatus according to this embodiment.

The ultrasonic diagnostic apparatus according to this embodiment has a function of simultaneously displaying images in a plurality of operation modes including the Doppler mode, as in the Triplex mode. A description will be made below assuming that the ultrasonic diagnostic apparatus according to this embodiment simultaneously displays images in the plurality of operation modes, that is, the B mode, the color mode, and the Doppler mode. The B mode is a mode to display a two-dimensional morphological image (B-mode image). The color mode is a mode to display a two-dimensional blood flow image (color Doppler mode image). The Doppler mode is a mode to display a Doppler waveform (Doppler spectrum image).

Note that the ultrasonic diagnostic apparatus according to this embodiment employs a scan method (segment scan) of transmitting an ultrasonic wave corresponding to the Doppler mode continuously for a predetermined period and then transmitting ultrasonic waves corresponding to the B mode and the color mode. According to the segment scan, a Doppler waveform in the Doppler mode is generated by interpolation when transmitting the ultrasonic waves corresponding to the B mode and the color mode.

As shown in FIG. 1, the ultrasonic diagnostic apparatus according to this embodiment includes an ultrasonic probe 10, a transmission/reception processing unit 20, a signal processing unit 30, a DSC (Digital Scan Converter) 40, a display unit 50, a pulsatory detection unit 60, an input unit 70, and a control unit 80.

The ultrasonic probe 10 includes a plurality of piezoelectric vibrators each of which generates an ultrasonic wave upon receiving a driving signal from the transmission/reception processing unit 20 and converts a reflected wave from a subject into an electrical signal, a matching layer provided on the piezoelectric vibrators, and a backing material that prevents the ultrasonic waves from propagating backward from the piezoelectric vibrators. When the ultrasonic probe 10 transmits an ultrasonic wave to the subject, the transmitted ultrasonic wave is sequentially reflected by a discontinuity surface of acoustic impedance of internal tissue and received by the ultrasonic probe 10 as an echo signal. The echo signal is supplied to the transmission/reception processing unit 20. Note that the amplitude of this echo signal depends on an acoustic impedance difference on the discontinuity surface by which the echo signal is reflected. The echo signal generated when an ultrasonic pulse is reflected by, for example, a moving blood flow or the surface of a cardiac wall or the like is subjected to a frequency shift depending on the velocity component of the moving body in the ultrasonic transmission direction due to the Doppler effect.

The transmission/reception processing unit 20 repetitively transmits/receives an ultrasonic wave (beam) via the ultrasonic probe 10 in accordance with changes in parameters related to a scan sequence (to be described later). The transmission/reception processing unit 20 includes a transmission processing unit 21 and a reception processing unit 22.

The transmission processing unit 21 transmits ultrasonic waves corresponding to the above-described B mode, color mode, and Doppler mode to the subject via the ultrasonic probe 10. The transmission processing unit 21 includes a pulse generator, a transmission delay unit, and a pulser (neither are shown). The pulse generator repeatedly generates rate pulses for the formation of transmission ultrasonic waves at a predetermined rate frequency fr Hz (period: 1/fr sec). The transmission delay unit gives the rate pulse of each channel a delay time necessary to focus an ultrasonic wave into a beam in accordance with each channel and decide transmission directivity. The pulser applies a driving pulse to the ultrasonic probe 10 at the timing based on the rate pulse for each channel.

The reception processing unit 22 receives an ultrasonic wave reflected by the subject via the ultrasonic probe 10 as an echo signal concerning a scan plane. The reception processing unit 22 includes a preamplifier, a reception delay unit, and an adder (neither are shown). The preamplifier amplifies an echo signal received via the ultrasonic probe 10 for each channel. The reception delay unit gives the amplified echo signal a delay time necessary to decide reception directivity. After that, the adder performs addition processing. With this addition, a reflection component from a direction corresponding to the reception directivity of the echo signal is enhanced, and a comprehensive beam of ultrasonic transmission/reception is formed by the transmission directivity and the reception directivity.

The signal processing unit 30 performs a plurality of ultrasonic signal processes corresponding to the plurality of operation modes based on echo signals from the reception processing unit 22. More specifically, the signal processing unit 30 includes a B-mode processing unit 31, a color mode processing unit 32, and a Doppler mode processing unit 33.

The B-mode processing unit 31 performs B-mode processing of an echo signal (an echo signal obtained by transmitting/receiving an ultrasonic wave corresponding to the B mode) from the reception processing unit 22. More specifically, the B-mode processing unit 31 performs envelope detection of the echo signal from the reception processing unit 22 and logarithmically compresses the echo signal that has undergone the envelope detection. Data of a B-mode image that expresses the intensity of the echo signal by a luminance is thus generated. The data of the B-mode image generated by the B-mode processing unit 31 is supplied to the DSC 40.

The color mode processing unit 32 performs color Doppler mode processing of an echo signal (an echo signal obtained by transmitting/receiving an ultrasonic wave corresponding to the color mode) from the reception processing unit 22 and generates data of a color mode image in a region of interest. More specifically, the color mode processing unit 32 performs quadrature detection of the echo signal from the reception processing unit 22. Next, the color mode processing unit 32 performs, by autocorrelation, frequency analysis of the echo signal that has undergone the quadrature detection. The color mode processing unit 32 calculates the average flow velocity value, the variance, and the like of a blood flow at each point of the sample by frequency analysis. The color mode processing unit 32 generates data of a color Doppler mode image that expresses the calculated average flow velocity value or variance by a color. The color mode processing unit 32 also calculates the power value of the blood flow based on the echo signal that has undergone the quadrature detection. The color mode processing unit 32 generates data of a color Doppler mode image that expresses the calculated power value by a color. The data of the color Doppler mode image generated by the color mode processing unit 32 is supplied to the DSC 40.

The Doppler mode processing unit 33 performs Doppler mode processing of an echo signal (an echo signal obtained by transmitting/receiving an ultrasonic wave corresponding to the Doppler mode) from the reception processing unit 22 and generates data of a Doppler waveform (Doppler spectrum image) in a range gate. More specifically, the Doppler mode processing unit 33 performs quadrature detection of the echo signal from the reception processing unit 22. The Doppler mode processing unit 33 extracts a signal in a preset range gate from the echo signal that has undergone the quadrature detection, performs spectrum analysis of the signal by FFT (Fast Fourier Transform), and calculates the flow velocity value (flow velocity spectrum). The Doppler mode processing unit 33 generates data of a Doppler waveform representing the time-rate change in the flow velocity spectrum. The data of the Doppler waveform generated by the Doppler mode processing unit 33 is supplied to the DSC 40.

The DSC 40 converts the data of the B-mode image from the B-mode processing unit 31 into image data displayable by the display unit 50. The DSC 40 also converts the data of the color Doppler mode image from the color mode processing unit 32 into image data displayable by the display unit 50. Similarly, the DSC 40 converts the data of the Doppler waveform from the Doppler mode processing unit 33 into image data displayable by the display unit 50.

The display unit 50 displays the B-mode image, the color Doppler mode image, and the Doppler waveform from the DSC 40 simultaneously on a display device in a superimposed manner. As the display device, for example, a CRT display, a liquid crystal display, an organic EL display, a plasma display, or the like is usable.

The pulsatory detection unit 60 detects the pulsatory of the blood flow of the subject corresponding to the scan plane based on, for example, the Doppler waveform and the like. More specifically, the pulsatory detection unit 60 determines whether the blood flow of the subject corresponding to the scan plane is a pulsating blood flow that temporally changes the flow velocity along with the heartbeat (to be referred to as a pulsating flow hereinafter) or a blood flow having a predetermined flow velocity (to be referred to as a steady flow hereinafter). The result of determination by the pulsatory detection unit 60 is sent to the control unit 80.

The input unit 70 inputs, to the control unit 80, various kinds of commands or information input by the user via an input device. More specifically, the input unit 70 inputs an instruction to start or end ultrasonic scan. The input unit 70 also inputs the position of the region of interest for the color mode or the position of the range gate for the Doppler mode. As the input device, for example, a keyboard, a mouse, various kinds of buttons, a touch panel, or the like can appropriately be used.

The control unit 80 functions as the main unit of the ultrasonic diagnostic apparatus. More specifically, the control unit 80 reads out a control program from a storage unit (not shown), extracts it on the memory of its own, and controls the respective units in accordance with the extracted control program.

The control unit 80 also changes parameters related to the above-described scan sequence in accordance with the pulsatory detected by the pulsatory detection unit 60. The control unit 80 thus optimizes the qualities of the B-mode image, the color Doppler mode image, and the Doppler waveform simultaneously displayed in the above-described Triplex mode. More specifically, the control unit 80 changes the ratio of transmission of the ultrasonic wave corresponding to the Doppler mode to transmission of the ultrasonic waves corresponding to the B mode and the color mode in the Triplex mode based on the determination result of the pulsatory detection unit 60. In other words, the control unit 80 changes the data distribution to the B mode, the color mode, and the Doppler mode. Note that when the data distribution to the B mode, the color mode, and the Doppler mode is changed, the ultrasonic wave corresponding to each mode is transmitted in accordance with the changed data distribution.

Figure 2:
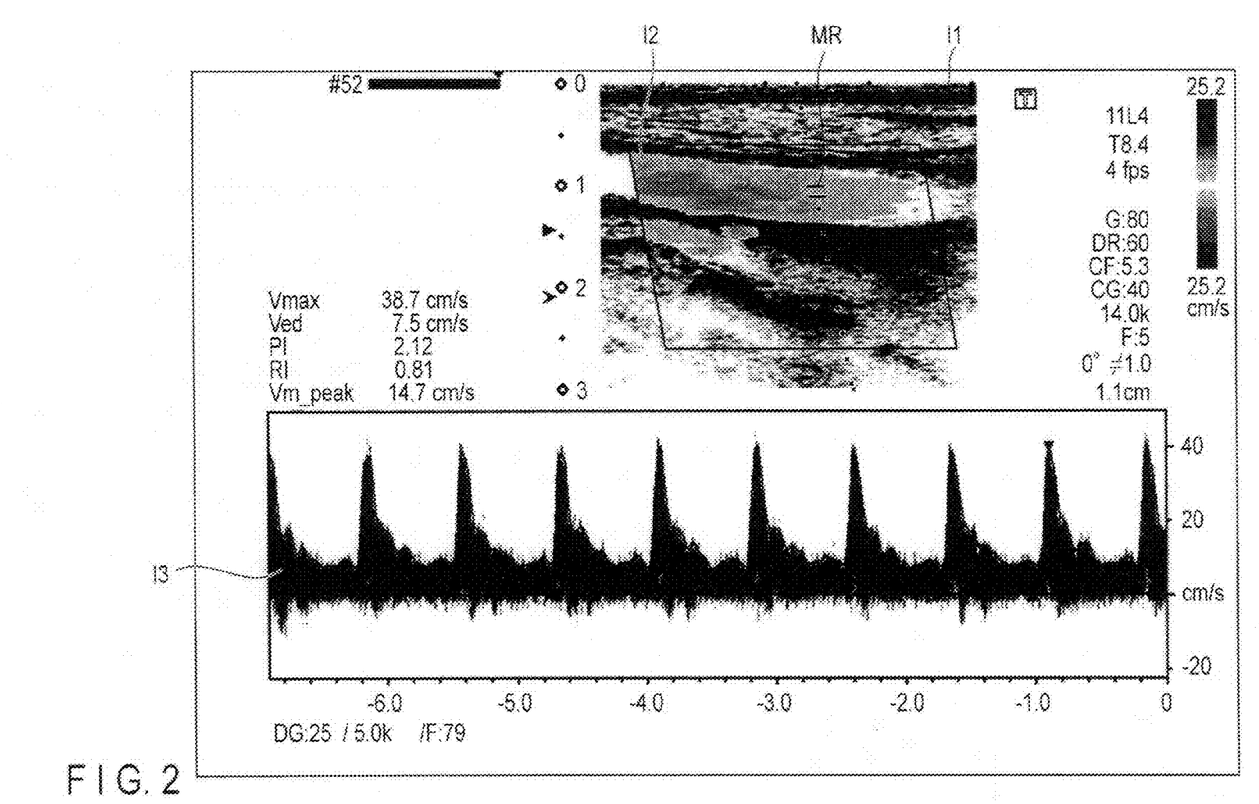
FIG. 2 is a view showing an example of an ultrasonic image displayed in the Triplex mode.

FIG. 2 shows an example of an ultrasonic image displayed in the above-described Triplex mode. As shown in FIG. 2, at the ultrasonic images in the Triplex mode, a B-mode image I1, a color Doppler mode image I2, and a Doppler waveform (Doppler spectrum image) I3 are simultaneously displayed. The B-mode image I1 is a two-dimensional morphological image concerning the B-mode scan plane. The color Doppler mode image I2 is a two-dimensional blood flow image in the region of interest, and is superimposed on the region of interest of the B-mode image I1. Note that a mark MR representing the position of the Doppler range gate is superimposed on the B-mode image I1. On the other hand, the Doppler waveform I3 is displayed under the B-mode image I1. The Doppler waveform I3 represents the Doppler spectrum in the range gate indicated by the mark MR. The Doppler waveform is a graph formed by plotting the blood flow velocity along the ordinate and time along the abscissa. In other words, the Doppler waveform represents the time-rate change in the blood flow velocity value of the subject corresponding to the scan plane. Typically, the B-mode image I1, the color Doppler mode image I2, and the Doppler waveform I3 are generated and displayed in real time.

The processing procedure of the ultrasonic diagnostic apparatus according to this embodiment will be described next with reference to the flowchart of FIG. 3.

First, the ultrasonic diagnostic apparatus starts scan in the above-described Triplex mode (scan in the above-described segment scan) to simultaneously display the images in the B mode, the color mode, and the Doppler mode (step S1). Note that according to the segment scan, an ultrasonic wave corresponding to the Doppler mode is transmitted continuously for a predetermined period, and then, ultrasonic waves corresponding to the B mode and the color mode are transmitted, as described above. In this case, the scan in the Triplex mode starts based on, for example, preset parameters (the data distribution to the B mode, the color mode, and the Doppler mode) related to the scan sequence. The B-mode image, the color Doppler mode image, and the Doppler waveform are thus displayed simultaneously on, for example, the display unit 50.

The examiner (operator) can provide, to the ultrasonic diagnostic apparatus, an instruction (to be referred to as an optimization instruction hereinafter) to optimize the qualities of the images in the B mode, the color mode, and the Doppler mode (the qualities of the B-mode image, the color Doppler mode image, and the Doppler waveform) simultaneously displayed in the Triplex mode by, for example, operating the ultrasonic diagnostic apparatus.

The input unit 70 inputs the optimization instruction in accordance with the operation of the examiner (step S2). The operations of the examiner for the optimization instruction include, for example, an operation of turning on the Quick Scan for Doppler switch. Note that the Quick Scan for Doppler is a technique of optimizing the flow velocity range, Baseline, and the like by the Doppler waveform. In this example, the optimization instruction is input by turning on the Quick Scan for Doppler switch, as described above. However, for example, a button configured to simply input the optimization instruction may be provided, and the optimization instruction may be input in accordance with an operation of pressing the button.

When the optimization instruction is input, the pulsatory detection unit 60 traces the Doppler waveform (past Doppler waveform) representing the time-rate change in the flow velocity value of the blood flow of the subject corresponding to the scan plane (to be simply referred to as the blood flow of the subject hereinafter) (step S3). Note that the past Doppler waveform includes, for example, the Doppler waveform obtained after the scan started in step S1 described above (before the Quick Scan for Doppler switch is turned on).

Next, the pulsatory detection unit 60 measures the time-rate change in the Doppler waveform from the data of the traced Doppler waveform. The pulsatory detection unit 60 determines, based on the measured time-rate change in the Doppler waveform, whether the change amount of the flow velocity value per unit time is equal to or larger than a predetermined value (to be referred to as a threshold hereinafter) (step S4).

Upon determining that the change amount of the flow velocity value is equal to or larger than the threshold (YES in step S4), the pulsatory detection unit 60 determines the blood flow of the subject as the pulsating flow and sends the determination result to the control unit 80.

When the blood flow of the subject is the pulsating flow, the control unit 80 increases the ratio of transmission of the ultrasonic wave corresponding to the Doppler mode and decreases the ratio of transmission of the ultrasonic waves corresponding to the remaining operation modes (B mode and color mode). That is, the control unit 80 changes the data distribution to the respective operation modes so as to increase the number of data of the Doppler mode and decrease that of the B mode and the color mode (step S5).

On the other hand, upon determining that the change amount of the flow velocity value is not equal to or larger than the threshold (NO in step S4), the pulsatory detection unit 60 determines the blood flow of the subject as the steady flow and sends the determination result to the control unit 80.

When the blood flow of the subject is the steady flow, the control unit 80 decreases the ratio of transmission of the ultrasonic wave corresponding to the Doppler mode and increases the ratio of transmission of the ultrasonic waves corresponding to the remaining operation modes (B mode and color mode). That is, the control unit 80 changes the data distribution to the respective operation modes so as to decrease the number of data of the Doppler mode and increase that of the B mode and the color mode (step S6).

When the process of step S5 or S6 described above is executed, the ultrasonic diagnostic apparatus resumes the scan (scan in the Triplex mode) using the changed data distribution (step S7).

Note that the above-described increase/decrease in the number of data of the Doppler mode may be implemented by changing the conditions such as the PRF (Pulse Repetition Frequency) and parallel simultaneous reception of the B mode, and the PRF, parallel simultaneous reception, and the number of ensembles of the color mode. More specifically, when the blood flow of the subject is the pulsating flow, the conditions are changed by, for example, raising the PRF of the B mode, turning on the parallel simultaneous reception of the B mode, raising the PRF of the color mode, turning on the parallel simultaneous reception of the color mode, or decreasing the number of ensembles of the color mode. This can raise the frame rate of the B mode and the color mode and increase the number of data of the Doppler mode instead. Note that in this case, the qualities of the B-mode image and the color Doppler mode image degrade.

In this example, the optimization instruction is input in accordance with the operation of the examiner, as described above. However, for example, the processing from step S3 described above may be executed as needed at a predetermined interval without the operation of the examiner.

Optimization of the qualities of the B-mode image, the color Doppler mode image, and the Doppler waveform simultaneously displayed in the Triplex mode of the ultrasonic diagnostic apparatus according to this embodiment will briefly be described below.

Figure 4:
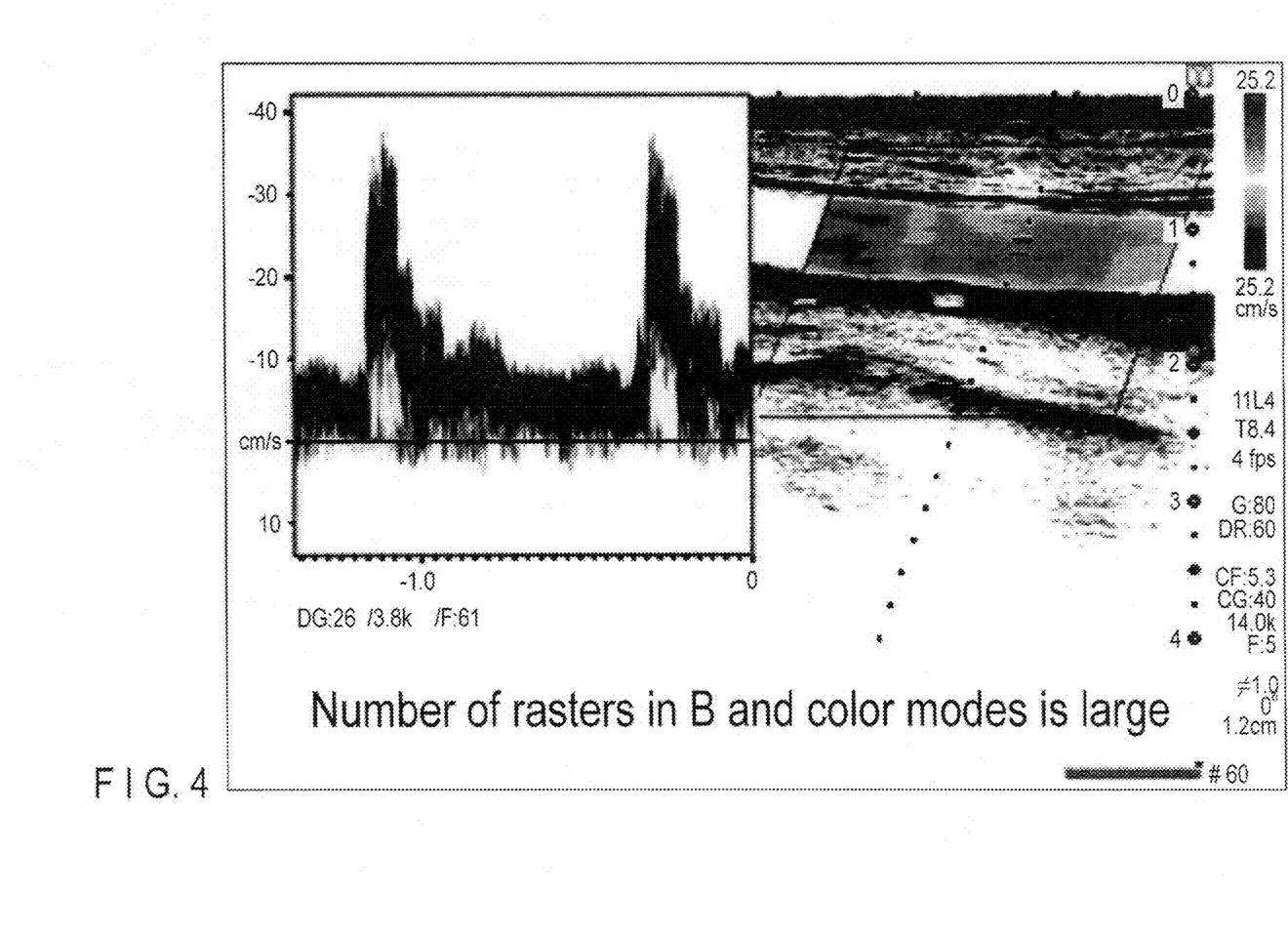
FIG. 4 is a view showing an example of an ultrasonic image displayed when the blood flow of a subject corresponding to a scan plane is a pulsating flow, and the number of data of the Doppler mode is small.
Figure 5:
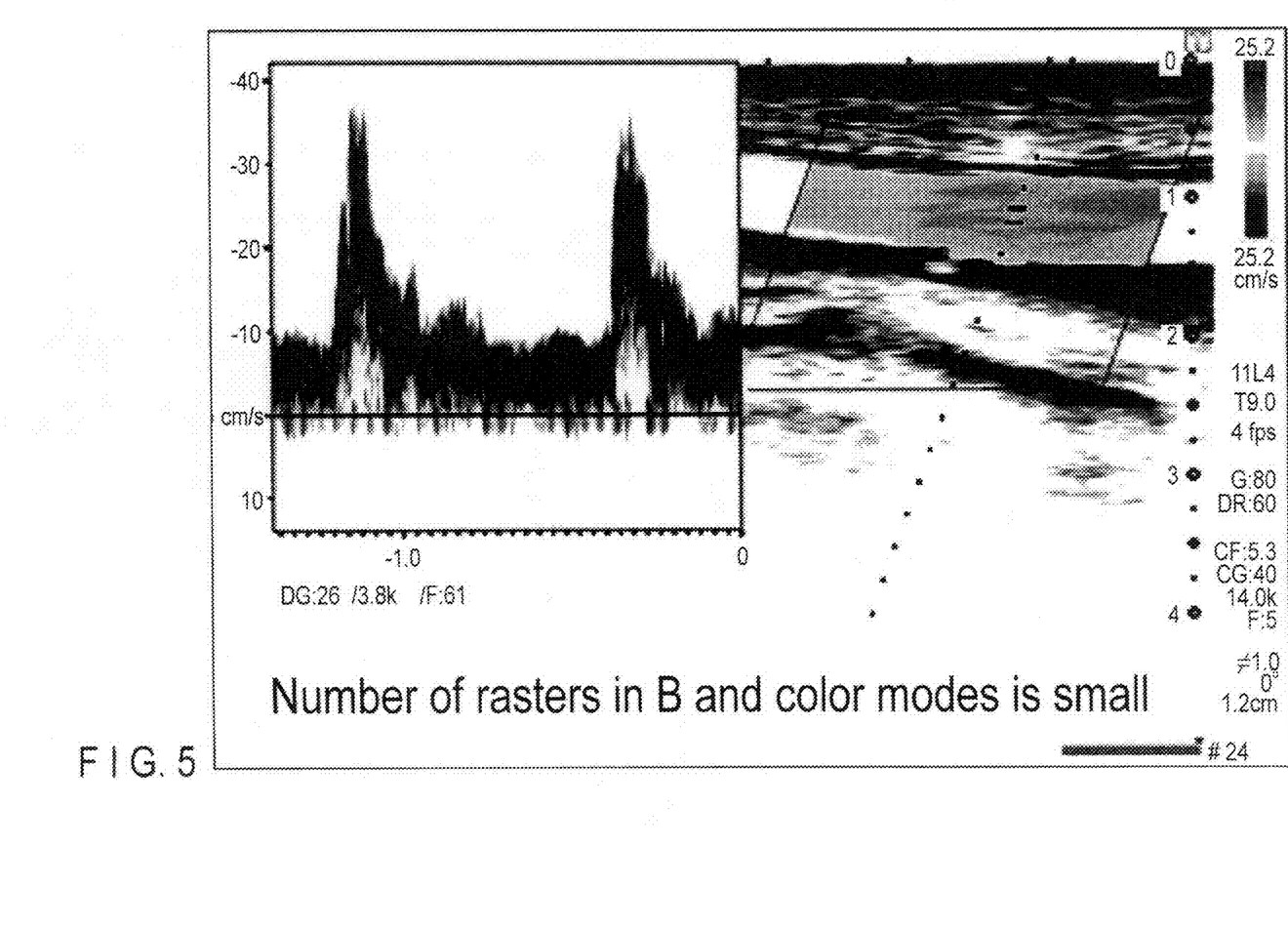
FIG. 5 is a view showing an example of an ultrasonic image displayed when the blood flow of a subject corresponding to a scan plane is a pulsating flow, and the number of data of the Doppler mode is large.
Figure 6:
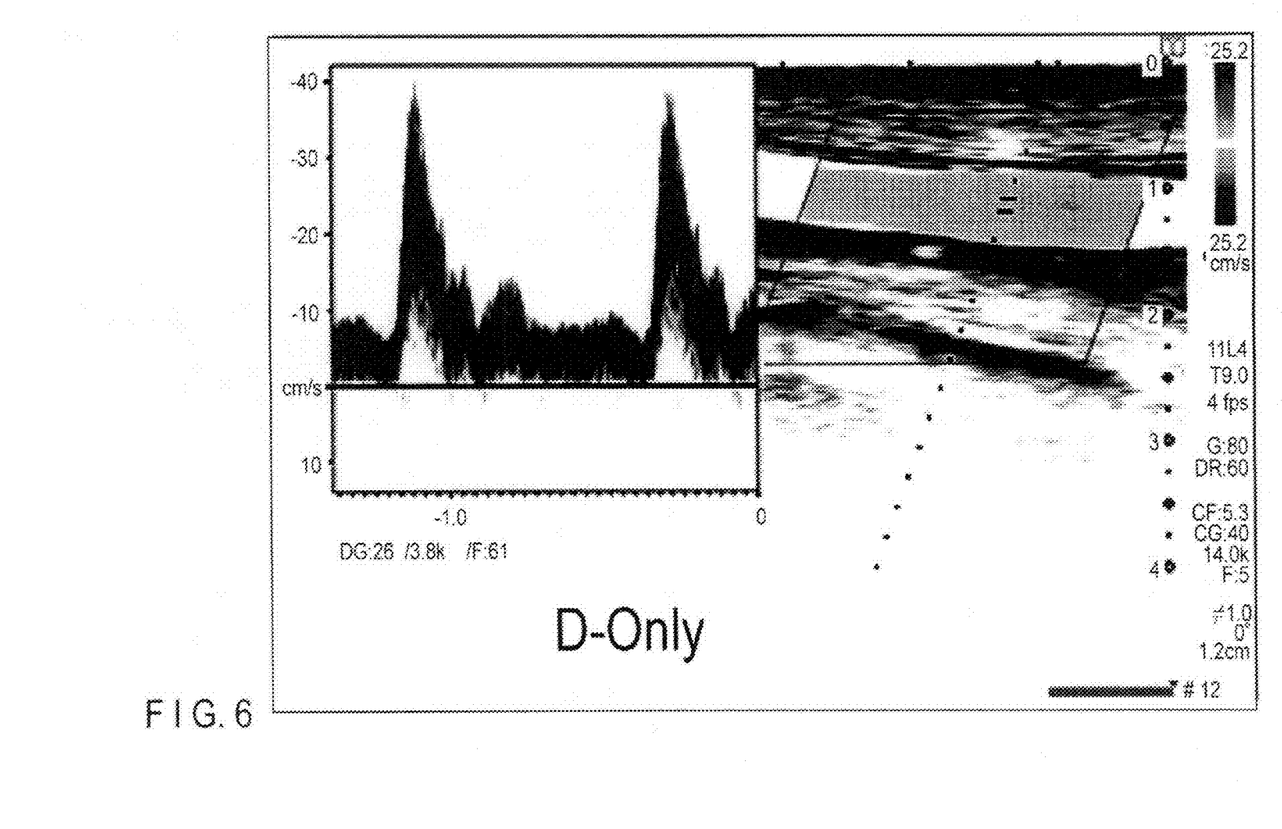
FIG. 6 is a view showing an example of an ultrasonic image displayed when the blood flow of a subject corresponding to a scan plane is a pulsating flow, and the ultrasonic diagnostic apparatus is operated only in the Doppler mode.

FIGS. 4, 5, and 6 show examples of ultrasonic images displayed in the Triplex mode when the blood flow of the subject corresponding to the scan plane is the pulsating flow. Note that FIG. 4 shows an ultrasonic image displayed when the number of data of the Doppler mode is small, and the number of data (number of rasters) of the B mode and the color mode is large. FIG. 5 shows an ultrasonic image displayed when the number of data of the Doppler mode is large, and the number of data (number of rasters) of the B mode and the color mode is small. FIG. 6 shows an ultrasonic image displayed when the ultrasonic diagnostic apparatus is operated only in the Doppler mode.

The Doppler waveforms shown in FIGS. 4 and 5 are compared. The Doppler waveform obtained by decreasing the number of data of the Doppler mode (that is, the Doppler waveform shown in FIG. 4) noticeably degrades as compared to the Doppler waveform shown in FIG. 6. For this reason, when the blood flow of the subject corresponding to the scan plane is the pulsating flow, the number of data of the Doppler mode needs to be increased to suppress the degradation in the Doppler waveform.

Figure 7:
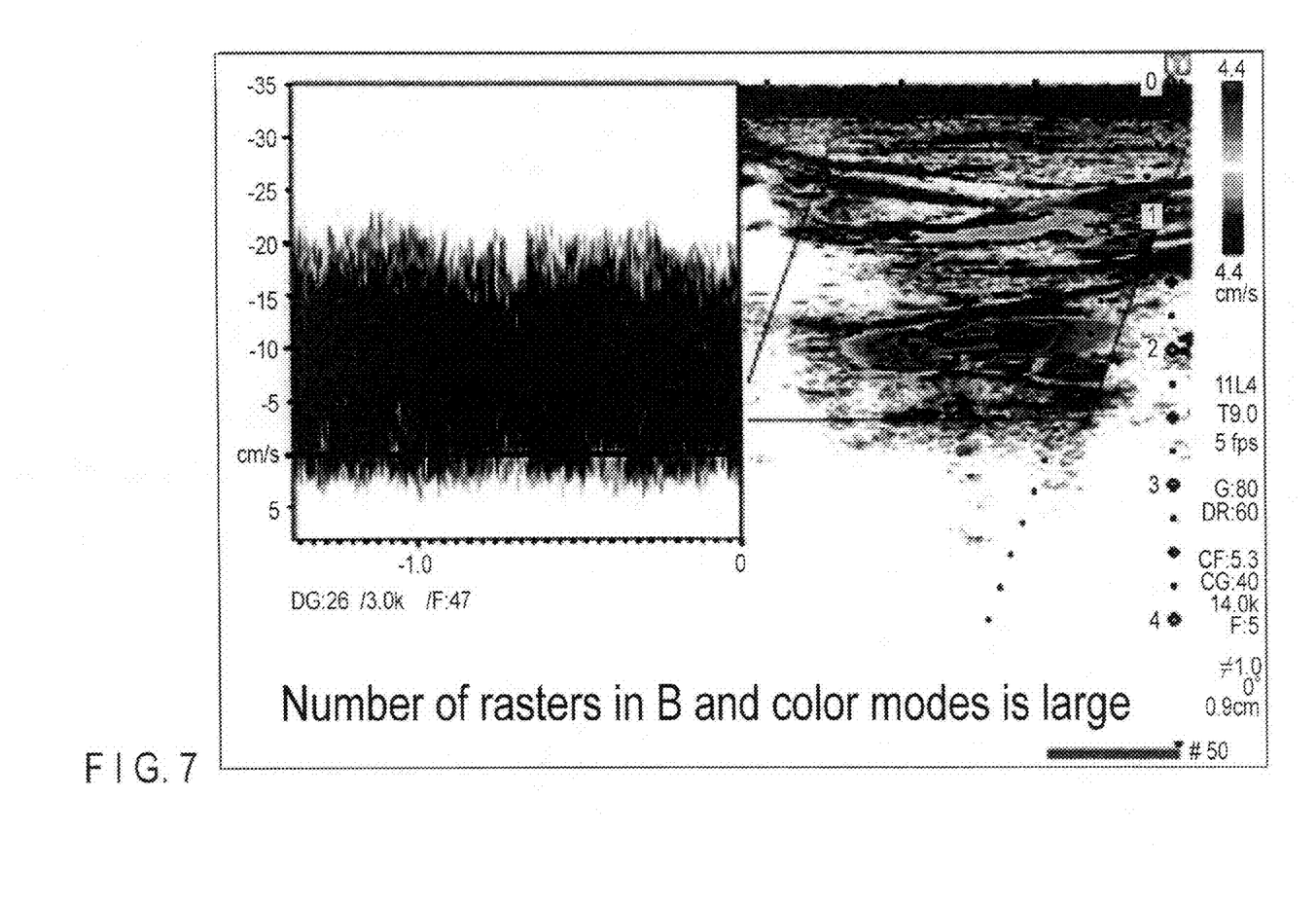
FIG. 7 is a view showing an example of an ultrasonic image displayed when the blood flow of a subject corresponding to a scan plane is a steady flow, and the number of data of the Doppler mode is small.
Figure 8:
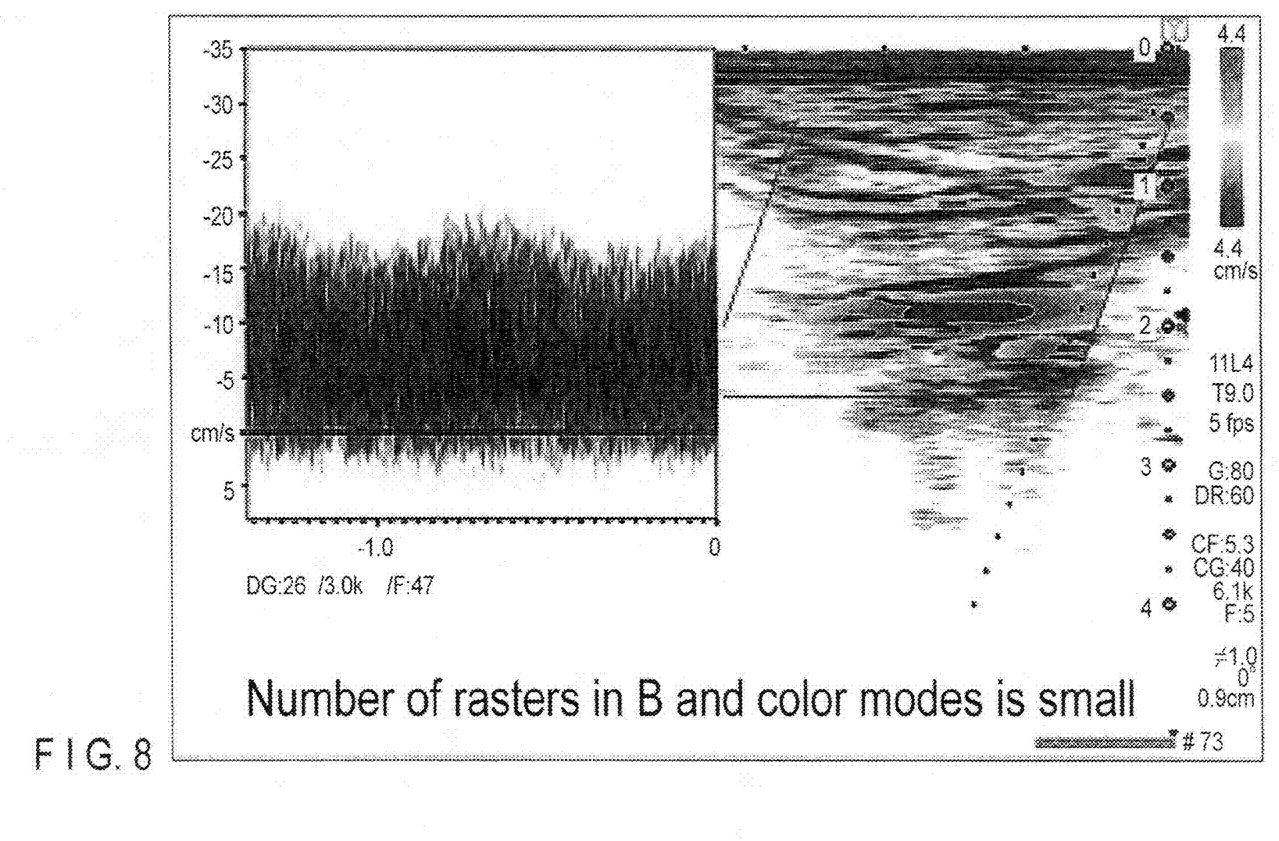
FIG. 8 is a view showing an example of an ultrasonic image displayed when the blood flow of a subject corresponding to a scan plane is a steady flow, and the number of data of the Doppler mode is large.
Figure 9:
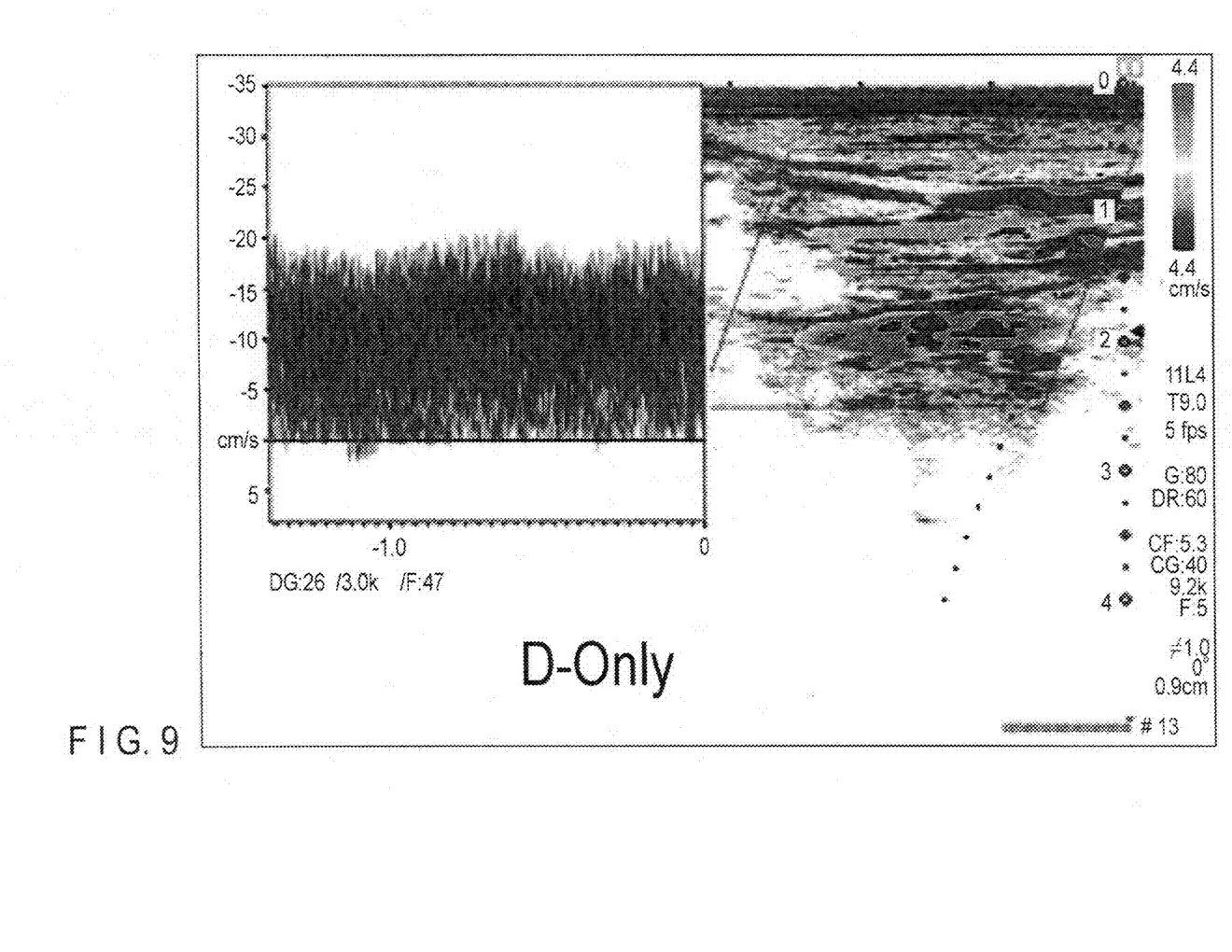
FIG. 9 is a view showing an example of an ultrasonic image displayed when the blood flow of a subject corresponding to a scan plane is a steady flow, and the ultrasonic diagnostic apparatus is operated only in the Doppler mode.

On the other hand, FIGS. 7, 8, and 9 show examples of ultrasonic images displayed in the Triplex mode when the blood flow of the subject corresponding to the scan plane is the steady flow. Note that FIG. 7 shows an ultrasonic image displayed when the number of data of the Doppler mode is small, and the number of data (number of rasters) of the B mode and the color mode is large. FIG. 8 shows an ultrasonic image displayed when the number of data of the Doppler mode is large, and the number of data (number of rasters) of the B mode and the color mode is small. FIG. 9 shows an ultrasonic image displayed when the ultrasonic diagnostic apparatus is operated only in the Doppler mode.

The Doppler waveforms shown in FIGS. 7 and 8 are compared. The degradation in the Doppler waveform is unnoticeable as compared to the Doppler waveform shown in FIG. 9 even when the number of data of the Doppler mode is decreased. For this reason, when the blood flow of the subject corresponding to the scan plane is the steady flow, the number of data of the Doppler mode is decreased, and the number of data of the B mode and the color mode is increased to improve the qualities of the B-mode image and the color Doppler mode image.

Data distribution to the B mode, the color mode, and the Doppler mode will be described here in detail for a case in which the blood flow of the subject corresponding to the scan plane is the pulsating flow and a case in which the blood flow of the subject is the steady flow.

Figure 10:
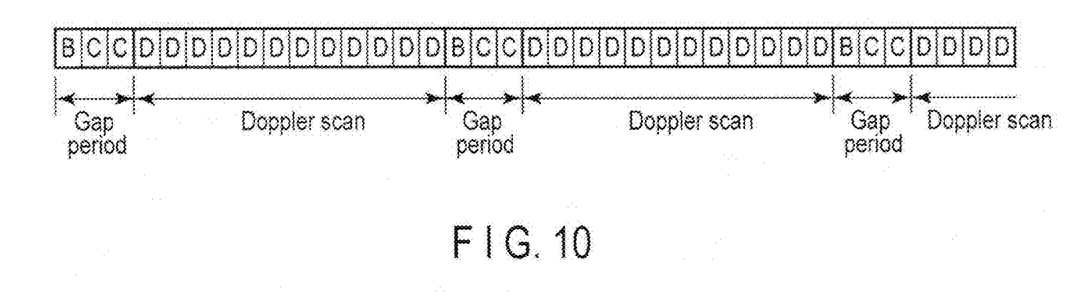
FIG. 10 is a view showing an example of data distribution to the respective operation modes when the blood flow of a subject corresponding to a scan plane is a pulsating flow.
Figure 11:
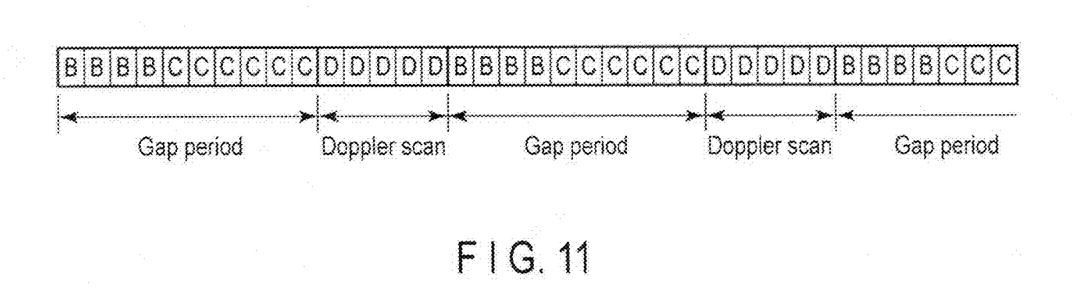
FIG. 11 is a view showing an example of data distribution to the respective operation modes when the blood flow of a subject corresponding to a scan plane is a steady flow.

FIG. 10 shows an example of data distribution to the respective operation modes when the blood flow of the subject corresponding to the scan plane is the pulsating flow. FIG. 11 shows an example of data distribution to the respective operation modes when the blood flow of the subject corresponding to the scan plane is the steady flow.

When the blood flow of the subject corresponding to the scan plane is the pulsating flow, the number of data of the Doppler mode is increased, and the period (gap period) in which the ultrasonic wave corresponding to the Doppler mode is not transmitted is shortened, as shown in FIG. 10. In this way, the degradation in the quality of the Doppler waveform in the Doppler mode is suppressed. More specifically, the number of rasters of the B mode is set to 150, the number of rasters of the color mode is set to 70, and the number of data of the Doppler mode is set to 128 (data).

On the other hand, when the blood flow of the subject corresponding to the scan plane is the steady flow, the number of data of the Doppler mode is decreased, and the period (gap period) in which the ultrasonic wave corresponding to the Doppler mode is not transmitted is prolonged, as shown in FIG. 11. In this way, the number of data of the B mode and the color mode is increased to improve the qualities of the B-mode image and the color Doppler mode image. More specifically, the number of rasters of the B mode is set to 300, the number of rasters of the color mode is set to 140, and the number of data of the Doppler mode is set to 64 (data).

As described above, in this embodiment, the ratio of transmission of the ultrasonic wave corresponding to the Doppler mode to transmission of the ultrasonic waves corresponding to the remaining operation modes is changed in accordance with the pulsatory (whether the blood flow is the pulsating flow or the steady flow) of the blood flow of the subject corresponding to the scan plane. This arrangement can automatically change the data distribution to the Doppler mode and the remaining operation modes. For this reason, the qualities of the images in the plurality of operation modes including the Doppler mode, which are simultaneously displayed as in the Triplex mode, can be optimized without causing the examiner to operate the IQ-balance switch or the like. That is, according to this embodiment, it is possible to save the examiner the time to, for example, adjust the image quality in the Triplex mode. Hence, the examination time can be shortened, and the burden on the subject or the like can be lightened.

In this embodiment, the time-rate change in the flow velocity value represented by the Doppler waveform is traced, and the pulsatory of the blood flow of the subject is detected based on the change amount of the flow velocity value per unit time (it is determined whether the blood flow is the pulsating flow or the steady flow), as described above. However, the pulsatory may be detected from a Doppler measurement index such as an RI (Resistance Index) or PI (Pulsatility Index).

The pulsatory may be detected based on, for example, the time-rate change in the B mode and the color mode. In the B mode, the correlation between the frames of the B-mode image is obtained. If the correlation between the frames is small, the blood flow can be determined as the pulsating flow. If the correlation between the frames is large, the blood flow can be determined as the steady flow. On the other hand, in the color mode, a certain region of interest is designated, and the time-rate change in the Doppler shift frequency of the color mode is measured. If the time-rate change in the Doppler shift frequency is large, the blood flow can be determined as the pulsating flow. If the time-rate change in the Doppler shift frequency is small, the blood flow can be determined as the steady flow.

In this embodiment, the Triplex mode in which the B-mode image, the color Doppler mode image, and the Doppler waveform are simultaneously displayed has mainly be described. However, this embodiment is applicable to any ultrasonic diagnostic apparatus for simultaneously displaying images in a plurality of operation modes including the Doppler mode. More specifically, the embodiment is also applicable to an ultrasonic diagnostic apparatus that operates in a duplex mode in which the B-mode image and the Doppler waveform are simultaneously displayed. In this case, the operation is the same as in the above-described Triplex mode except that the scan during the above-described gap period is done only in the B mode.

(Second Embodiment)

An ultrasonic diagnostic apparatus according to the second embodiment will be described next. A description will be made below assuming that the ultrasonic diagnostic apparatus according to this embodiment simultaneously displays images in a plurality of operation modes, that is, the B mode, the color mode, and the Doppler mode, as in the above-described first embodiment.

Note that the arrangement of the ultrasonic diagnostic apparatus according to this embodiment is the same as in the above-described first embodiment, and will be described with reference to FIG. 1 as needed. Points of difference from the above-described first embodiment will mainly be explained here.

In the above-described first embodiment, data distribution to the respective operation modes is changed in accordance with the result of determining whether the blood flow of a subject is the pulsating flow or the steady flow. In the second embodiment, however, the data distribution (the ratio of transmission of the ultrasonic wave corresponding to the Doppler mode) is further changed in accordance with the degree of pulsatory in the pulsating flow, unlike the above-described first embodiment.

Note that in the ultrasonic diagnostic apparatus according to this embodiment, a control unit 80 includes a table that holds, in advance, the ratio of transmission of the ultrasonic wave corresponding to the Doppler mode to transmission of the ultrasonic waves corresponding to the remaining operation modes (B mode and color mode) in association with the degree of pulsatory (that is, data distribution to the B mode, the color mode, and the Doppler mode). More specifically, the table provided in the control unit 80 holds data distribution (to be referred to as first data distribution hereinafter) to the respective operation modes corresponding to a pulsating flow having a high degree of pulsatory (to be referred to as a first pulsating flow hereinafter) in association with the index of the first pulsating flow. Similarly, the table provided in the control unit 80 holds data distribution (to be referred to as second data distribution hereinafter) to the respective operation modes corresponding to a pulsating flow having a low degree of pulsatory (to be referred to as a second pulsating flow hereinafter) in association with the index of the second pulsating flow. In addition, the table provided in the control unit 80 holds data distribution (to be referred to as third data distribution hereinafter) to the respective operation modes corresponding to a steady flow in association with the index of the steady flow. That is, in this embodiment, three kinds of IQ-balance are set in accordance with the degrees of pulsatory (first pulsating flow, second pulsating flow, and steady flow).

Note that the degradation in the Doppler waveform is noticeable in the first pulsating flow than in the second pulsating flow because of the higher degree of pulsatory. Hence, the ratio of transmission of the ultrasonic wave corresponding to the Doppler mode is higher in the first data distribution than in the second data distribution.

Figure 12:
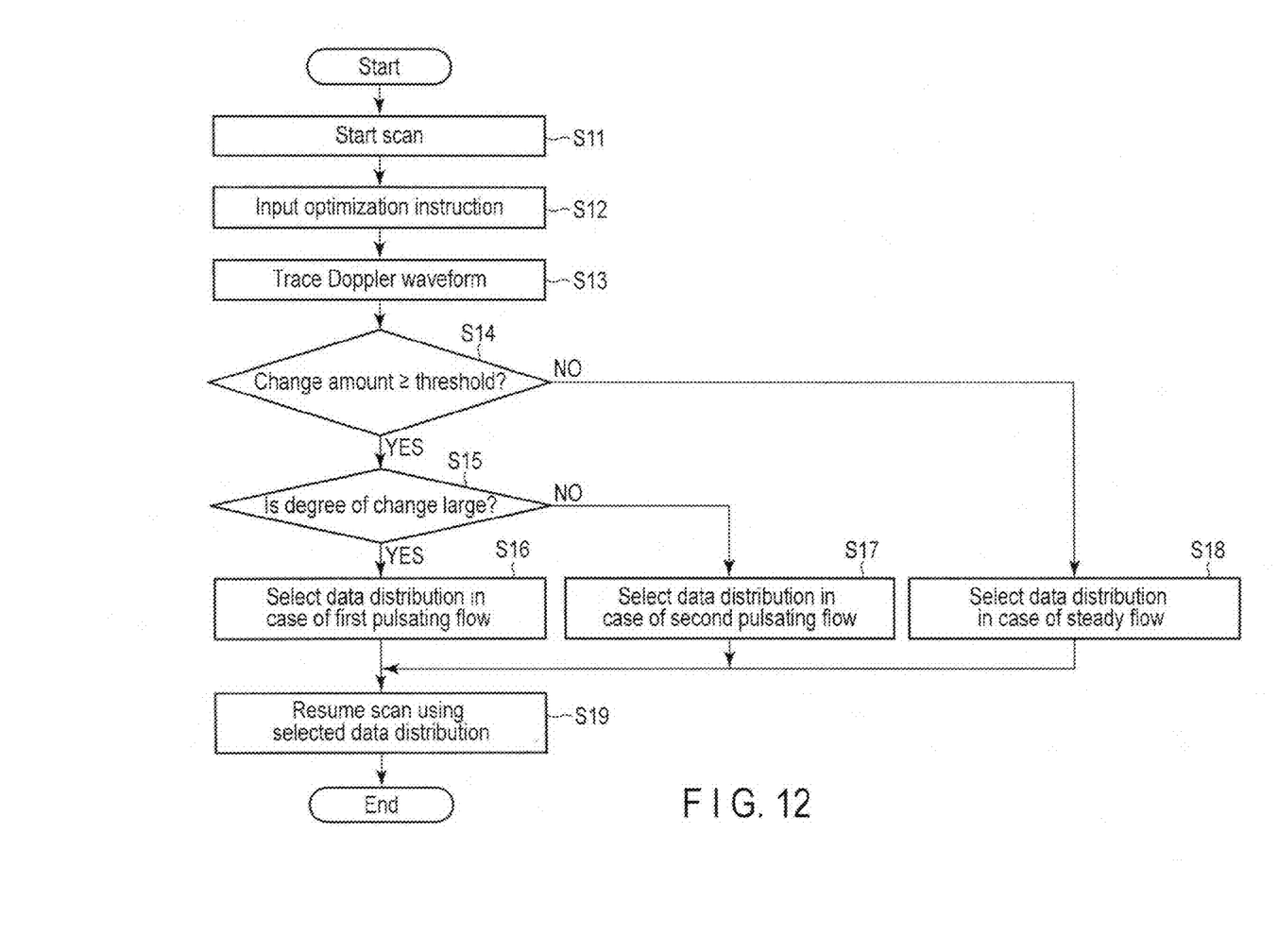
FIG. 12 is a flowchart showing the processing procedure of an ultrasonic diagnostic apparatus according to the second embodiment.

The operation of the ultrasonic diagnostic apparatus according to this embodiment will be described next. FIG. 12 is a flowchart showing the processing procedure of the ultrasonic diagnostic apparatus according to this embodiment.

Figure 3:
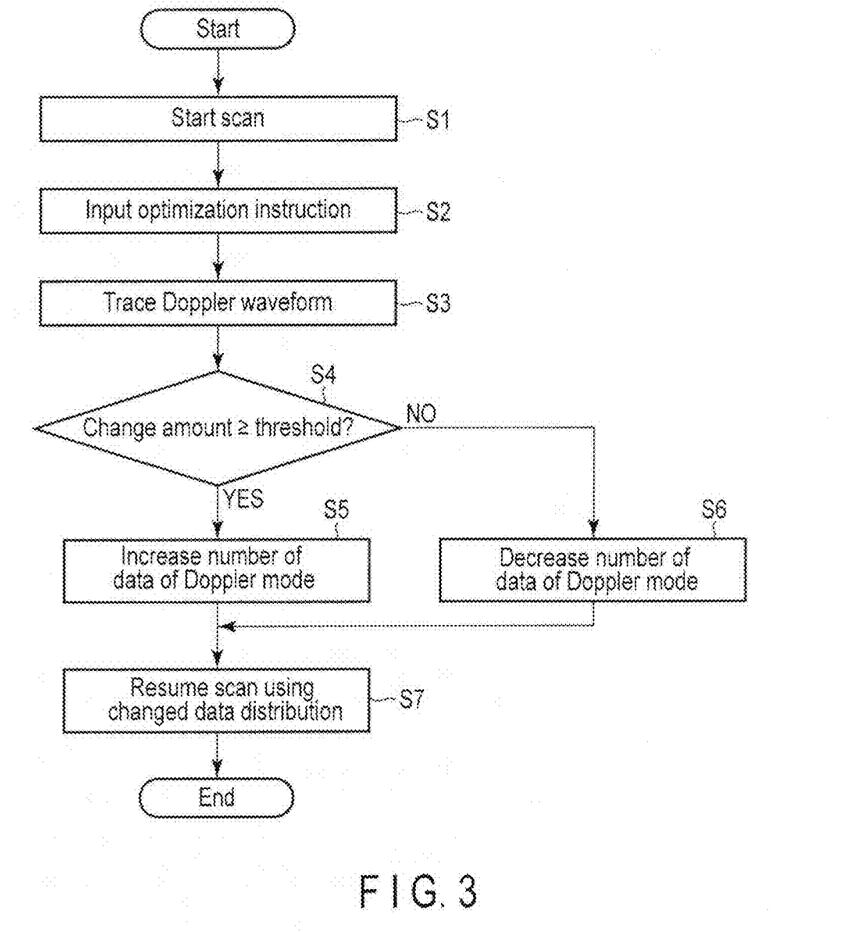
FIG. 3 is a flowchart showing the processing procedure of the ultrasonic diagnostic apparatus according to the embodiment.

First, the processes of steps S11 to S14 corresponding to the processes of steps S1 to S4 shown in FIG. 3 described above are executed.

Upon determining in step S14 that the change amount of the flow velocity value is equal to or larger than a threshold (to be referred to as a first threshold hereinafter), a pulsatory detection unit 60 compares the change amount of the flow velocity value with a threshold (to be referred to as a second threshold hereinafter) different from the first threshold, thereby determining whether the degree of the change in the flow velocity value is large (step S15).

Upon determining that the degree of the change in the flow velocity value is large (YES in step S15), the pulsatory detection unit 60 determines the blood flow of the subject as the first pulsating flow and sends the determination result to the control unit 80.

When the blood flow of the subject is the first pulsating flow, the control unit 80 looks up the table provided in it and selects the first data distribution (data distribution in case of the first pulsating flow) held in the table in association with (the index of) the first pulsating flow (step S16). Note that as an example of the first data distribution selected in step S16, the number of rasters of the B mode is set to 150, the number of rasters of the color mode is set to 70, and the number of data of the Doppler mode is set to 128 (data).

On the other hand, upon determining that the degree of the change in the flow velocity value is not large (NO in step S15), the pulsatory detection unit 60 determines the blood flow of the subject as the second pulsating flow and sends the determination result to the control unit 80.

When the blood flow of the subject is the second pulsating flow, the control unit 80 looks up the table provided in it and selects the second data distribution (data distribution in case of the second pulsating flow) held in the table in association with (the index of) the second pulsating flow (step S17). Note that as an example of the second data distribution selected in step S17, the number of rasters of the B mode is set to 200, the number of rasters of the color mode is set to 100, and the number of data of the Doppler mode is set to 96 (data). In the second data distribution, the number of data of the Doppler mode (the ratio of transmission of the ultrasonic wave corresponding to the Doppler mode) is smaller than in the above-described first data distribution.

Upon determining in step S14 that the change amount of the flow velocity value is not equal to or larger than the first threshold, the pulsatory detection unit 60 determines the blood flow of the subject as the steady flow and sends the determination result to the control unit 80.

When the blood flow of the subject is the steady flow, the control unit 80 looks up the table provided in it and selects the third data distribution (data distribution in case of the steady flow) held in the table in association with (the index of) the steady flow (step S18). Note that as an example of the third data distribution selected in step S18, the number of rasters of the B mode is set to 300, the number of rasters of the color mode is set to 140, and the number of data of the Doppler mode is set to 64 (data).

When the process of step S16, S17, or S18 described above is executed, the ultrasonic diagnostic apparatus resumes the scan (scan in the Triplex mode) using the selected data distribution (step S19).

As described above, in this embodiment, the ratio of transmission of the ultrasonic wave corresponding to the Doppler mode to transmission of the ultrasonic waves corresponding to the remaining operation modes (that is, the data distribution to the respective operation modes) held in the table prepared in advance is selected in association with the detected degree of pulsatory. The current data distribution to the respective operation modes is changed to the selected data distribution to the respective operation modes, thereby more specifically changing the settings in accordance with the degree of pulsatory, as compared to the above-described first embodiment.

According to the above-described embodiments, it is possible to provide an ultrasonic diagnostic apparatus capable of optimizing the qualities of images in a plurality of operation modes including the Doppler mode, which are simultaneously displayed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
    an ultrasonic probe;
    a transmission processing unit configured to transmit, to a subject via the ultrasonic probe, an ultrasonic wave corresponding to a Doppler mode to display a Doppler waveform representing a time-rate change in a flow velocity value of a blood flow of the subject and an ultrasonic wave corresponding to at least one of a B mode and a color Doppler mode other than the Doppler mode;
    a reception processing unit configured to receive the ultrasonic wave reflected by the subject via the ultrasonic probe as an echo signal concerning a scan plane;
    a digital scan converter configured to generate a Doppler waveform related to the Doppler mode and at least one of a B-mode image related to the B mode and a color Doppler mode image related to the color Doppler mode based on the echo signal;
    a display configured to simultaneously display the Doppler waveform and at least one of the B-mode image and the color Doppler mode image;
    a detection unit configured to detect a pulsatory of the blood flow of the subject corresponding to the scan plane and determine in accordance with the degree of the detected pulsatory whether the blood flow of the subject corresponding to the scan plane is a pulsating flow that temporally changes a flow velocity along with the heartbeat or a steady flow having a predetermined flow velocity; and
    a control unit configured to increase a ratio of transmission of the ultrasonic wave corresponding to the Doppler mode upon determining that the blood flow of the subject is the pulsating flow, and decrease the ratio of transmission of the ultrasonic wave corresponding to the Doppler mode upon determining that the blood flow of the subject is the steady flow.

2. The apparatus according to claim 1, wherein the detection unit traces the time-rate change in the flow velocity value represented by the Doppler waveform, and detects the pulsatory based on whether a change amount of the flow velocity value per unit time is equal to or larger than a predetermined value.

3. The apparatus according to claim 1, wherein the detection unit detects the pulsatory in accordance with correlation between frames of the B-mode image.

4. The apparatus according to claim 1, wherein the detection unit detects the pulsatory in accordance with a time-rate change in a Doppler shift frequency obtained in the color mode.

5. The apparatus according to claim 1, further comprising a table configured to hold the ratio of transmission of the ultrasonic wave corresponding to the Doppler mode to transmission of the ultrasonic wave corresponding to at least one of the B mode and the color Doppler mode in advance in association with the degree of the pulsatory, and
    the control unit changes the ratio of transmission of the ultrasonic wave corresponding to the Doppler mode to transmission of the ultrasonic wave corresponding to at least one of the B mode and the color Doppler mode to the ratio held in the table in association with the degree of the detected pulsatory.

6. The apparatus according to claim 1, wherein the control unit changes the ratio of transmission of the ultrasonic wave corresponding to the Doppler mode to transmission of the ultrasonic wave corresponding to at least one of the B mode and the color Doppler mode by changing a repetition frequency and parallel simultaneous reception of the B mode, and the repetition frequency, parallel simultaneous reception, and the number of ensembles of the color mode.

7. The apparatus according to claim 1, wherein the detection unit detects the pulsatory in accordance with an instruction from an examiner.

8. The apparatus according to claim 1, wherein the detection unit detects the pulsatory at a predetermined interval.

* * * * *